(12) United States Patent
Inagaki

(10) Patent No.: US 6,645,157 B2
(45) Date of Patent: Nov. 11, 2003

(54) CUFF FOR BLOOD PRESSURE MONITOR

(75) Inventor: Takashi Inagaki, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 10/047,994

(22) Filed: Jan. 17, 2002

(65) Prior Publication Data

US 2002/0099299 A1 Jul. 25, 2002

(30) Foreign Application Priority Data

Jan. 23, 2001 (JP) ........................................ 2001-013921

(51) Int. Cl.[7] ................................................ A61B 5/02
(52) U.S. Cl. .................... 600/499; 600/485; 600/490
(58) Field of Search ........................ 600/485, 490–496, 600/499; D24/165

(56) References Cited

U.S. PATENT DOCUMENTS

| 4,549,550 A | * | 10/1985 | Kami | 600/499 |
|---|---|---|---|---|
| 4,790,325 A | * | 12/1988 | Lee | 600/490 |
| 4,901,732 A | * | 2/1990 | Williams | 600/499 |
| 5,228,448 A | * | 7/1993 | Byrd | 600/490 |
| 5,511,551 A | * | 4/1996 | Sano et al. | 600/499 |
| 5,595,180 A | * | 1/1997 | Ogura et al. | 600/499 |
| 5,840,037 A | * | 11/1998 | Tochikubo et al. | 600/499 |
| 5,885,220 A | * | 3/1999 | Schaer | 426/39 |
| 6,379,310 B1 | * | 4/2002 | Mori et al. | 600/490 |

* cited by examiner

Primary Examiner—Eric F. Winakur
Assistant Examiner—Patricia C. Mallari
(74) Attorney, Agent, or Firm—Morrison & Foerster LLP

(57) ABSTRACT

To provide a cuff for a blood pressure monitor having a curled elastic member which is easily attached to an arm, does not make the subject feel pain when attached, and exhibits a characteristic of excellent fitting.

A curled elastic member 1A has one end portion 12 extending outward so as to enwind the other end portion 11 inward. Specifically, from the other end portion 11 to a position where the other end portion 11 is mutually opposite, the radius of curvature gently increases. From the mutually opposite portion to the one end portion 12, the radius of curvature largely increases.

7 Claims, 13 Drawing Sheets

FIG.10A
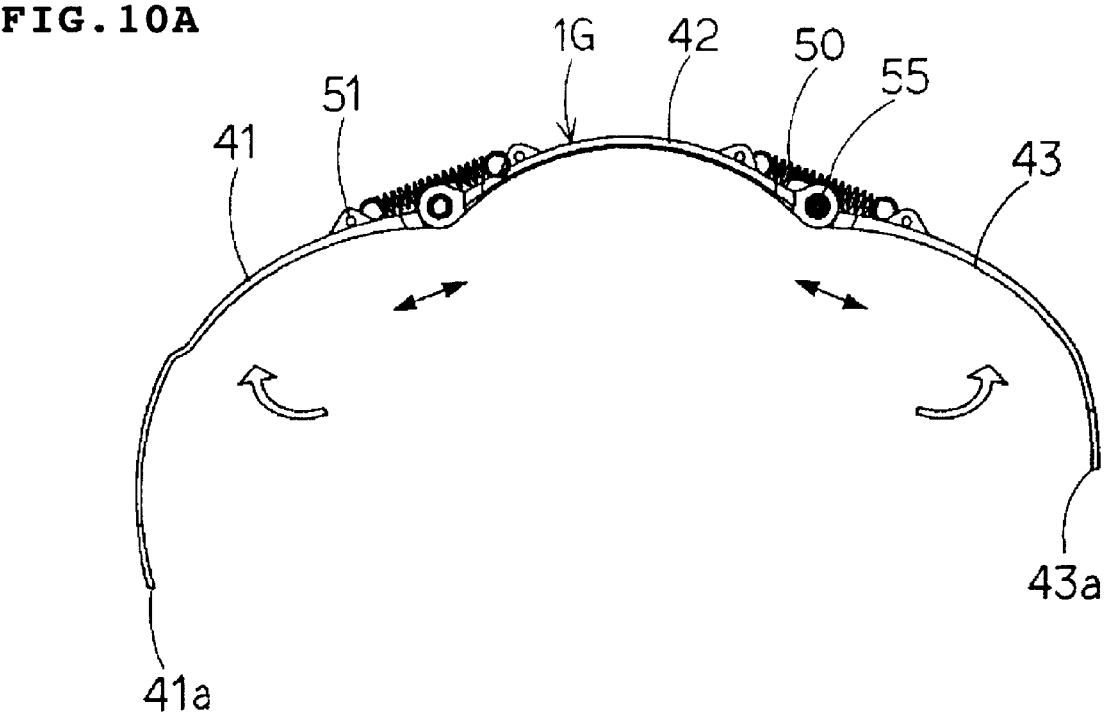
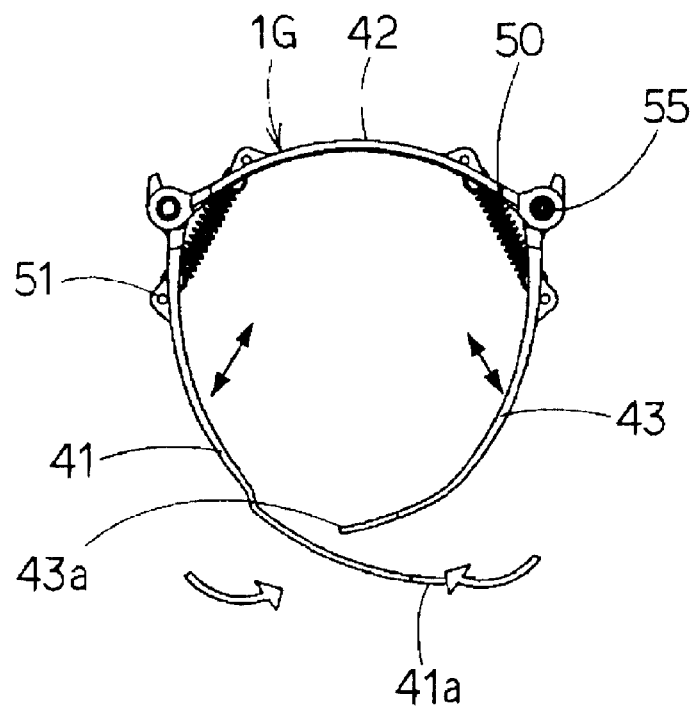
FIG.10B

CUFF FOR BLOOD PRESSURE MONITOR

BACKGROUND OF THE INVENTION

1. Field of the Invention

The present invention relates to a cuff for a blood pressure monitor and, more particularly, to a cuff characterized by a curled elastic member disposed on the outside of a bladder to hold a ring form of the cuff.

2. Description of the Related Art

As shown in FIG. 11 (perspective view) and FIG. 12 (sectional view), a cuff for a blood pressure monitor has generally a configuration such that a bladder 91 and a curled elastic member 92 are provided in a cloth bag 90. A tube 93 is connected to the bladder 91, and a velcro fastener 94 is attached on the outside of the cloth bag 90. The curled elastic member 92 is disposed on the outside of the bladder 91 to hold the cuff in a ring form by its elasticity. As shown in FIG. 13A, the curled elastic member 92 has an uniform thickness and has a sectional shape of a complete round in which a part thereof is a discontinuous portion 92a.

However, the curled elastic member 92 as shown in FIG. 13A has the following problems 1 to 3.

1. Operation of uncurling the curled elastic member 92 to be attached on an arm is not easy.

Since the sectional shape is a complete round, the curled elastic member 92 has to be uncurled and then attached on an arm. Specifically, in order to uncurl the curled elastic member 92, it has to be pulled with some strength. The user needs some experience to attach the elastic member 92 in the uncurled state onto his/her arm.

2. The end portions of the curled elastic member 92 cut into the flesh of the arm.

In the case of the curled elastic body 92 having the sectional shape of complete round, when it is attached around the arm, the edges of the discontinuous portion 92a cut into the flesh of the arm and the subject often feels pain. Particularly, in the case of a big arm, such a tendency is conspicuous.

3. The shape of the curled elastic member 92 cannot be altered according to the size and shape of an arm such as slender arm, big arm, tapered arm (arm of which size changes largely from the shoulder to the elbow), straight arm (arm of which size changes little from the shoulder to the elbow) or the like, so that the curled elastic member 92 is not easily fit to an arm.

This is because the thickness of the curled elastic member 92 is uniform and the sectional shape thereof is a complete round. Although the size and shape of an arm vary widely with the individual, the curled elastic member 92 does not have a form which can be easily fit to every one.

On the other hand, a curled elastic member having increased fitness which can be attached to an arm more easily has been proposed as shown in FIG. 13B (Japanese Unexamined Patent Publication No. 61-238229 (1987)). This curled elastic member 92' is formed so that its thickness gradually increases from the both ends (discontinuous portion 92'a) toward the center portion and, accordingly, the rigidity gradually increases. The thickness and rigidity are the maximum in the center portion.

However, even in the curled elastic member 92', since the thickness is simply gradually increased from the both ends toward the center portion, the shape is not flexibly altered to be adapted to various arms, and it has room for improvement. A provision of a curled elastic member having more excellent performance is awaited.

SUMMARY OF THE INVENTION

The present invention has been achieved by paying attention to such conventional problems and circumstances and an object of the present invention is to provide a cuff for a blood pressure monitor having a curled elastic member which can be easily attached to an arm, does not make the subject feel pain when attached, and exhibits the characteristic of excellent fitness.

In order to achieve the above-mentioned object, a cuff for a blood pressure monitor of the present invention having therein a bladder and a curled elastic member disposed on the outside of the bladder to hold a ring shape of the cuff, wherein one end portion of the curled elastic member is extended outward so as to enwind the other end portion inward.

In the curled elastic member, at the time of attachment to an arm, the one end portion extended outward is thrown over the arm, and the curled elastic member can be put on the arm while being largely uncurled. That is, the operation of uncurling the curled elastic member and the operation of attaching the curled elastic member to an arm can be simultaneously performed, so that the operation of attachment to an arm is easy. Since the curled elastic member has such a form that the one end portion is longer than the other end portion and the other end portion is enwinded inward, the end portions do not easily cut in the flesh of an arm when attached, so that the subject does not feel pain.

According to another embodiment of the curled elastic member, a sectional shape of the curled elastic member is approximately triangle and one end portion of the curled elastic member is extended. By the curled elastic member as well, equivalent action and effects can be obtained.

According to further another embodiment, the curled elastic member has a narrow portion in which width in the axial direction of an arm is partly narrowed or a thin portion in which thickness is partly reduced between an approximately center portion in the circumferential direction of the arm and both end portions. In this case, the elasticity and alteration in the shape can be adjusted by the narrow portion or the thin portion. That is, by the narrow portion or the thin portion, the curled elastic member (i.e., the cuff) gets easily to be twisted. Thus, the curled elastic member is fit more easily to an arm of any shape such as a straight arm or tapered arm.

Moreover, the narrow portion or thin portion is not provided as the both end portions of the curled elastic member, so that the rigidity of the both end portions is not reduced and an arm can be securely held by the both end portions. Furthermore, by not particularly providing the narrow portion as the both end portions of the curled elastic member, as compared with the case where the both end portions are narrowed, the subject does not have strange feeling such that the both end portions cut into the flesh of the arm.

In the case of the form in which the curled elastic member has the narrow portion, although the form may be used satisfactorily, it is preferable to construct a portion missed by narrowing the width to form the narrow portion by a thin portion which is thinner than the narrow portion. This is because that if the portion missed by the narrow portion exists, when the bladder is inflated, it is feared that the bladder is inflated from the side (missing portion) of the narrow portion to the surface side of the cuff so that the arm cannot be sufficiently pressed, and there is also the possibility such that, in a process of taking blood pressure data while changing air pressure, noise occurs due to inflation from the missing portion to the outside of the bladder so that blood pressure cannot be measured stably.

The configuration in which the missing portion generated due to the narrow portion is formed as the thin portion aims at obtaining an effect such that, while maintaining fitness by the both end portions, the curled elastic member is easily twisted so as to be fit to any of arms of various shapes such as straight arm or tapered arm.

The narrow portion may have a constant width in the circumferential direction of an arm or a width gradually reduced from the center portion toward both end portions.

According to further another embodiment, an inner circumferential face of the curled elastic member may have an approximately round shape and an outer circumferential face of the curled elastic member may have an approximately polygon shape. In other words, the curled elastic member has a sectional shape such that the round inner circumferential face is inscribed in the polygonal outer circumferential face (strictly, it is not inscribed). The curled elastic member is thick at corner portions of the polygon and is thin in the side portions. Therefore, the form in which the thickness of the curled elastic member is substantially changed is obtained. In a manner similar to the curled elastic member having the portion of which shape is altered, the shape can be altered in correspondence with variations in arms. The curled elastic member does not easily cut in the flesh of an arm and has an excellent fitness to an arm.

A curled elastic member having the structure quite different from that of the above-mentioned curled elastic member may be also used. The curled elastic member is formed by connecting a plurality of elastic pieces by hinges, and energizing means for energizing the elastic member in a direction of uncurling the elastic member when the elastic member is uncurled at a predetermined angle or more, and energizing the elastic member in a direction of curling the elastic member when the elastic member is curled at a predetermined angle or less is provided on the hinged portions of the respective elastic pieces.

In the curled elastic member, the energizing force to the uncurling direction and the energizing force to the curling direction are given by the energizing means rather than the elasticity of the elastic pieces. The energizing force changes by using uncurling of the elastic member at a predetermined angle as a branch point. That is, when the elastic member is largely uncurled at the time of attachment to an arm, it is automatically largely uncurled by the energizing means. When the elastic member is curled at the time of fixing to the arm, it is automatically curled by the energizing means and fits to the arm.

BRIEF DESCRIPTION OF THE DRAWINGS

FIGS. 10A and 10B are side views of the curled elastic member in an uncurled state and in a curled state, respectively;

DESCRIPTION OF THE PREFERRED EMBODIMENTS

Figure 12:
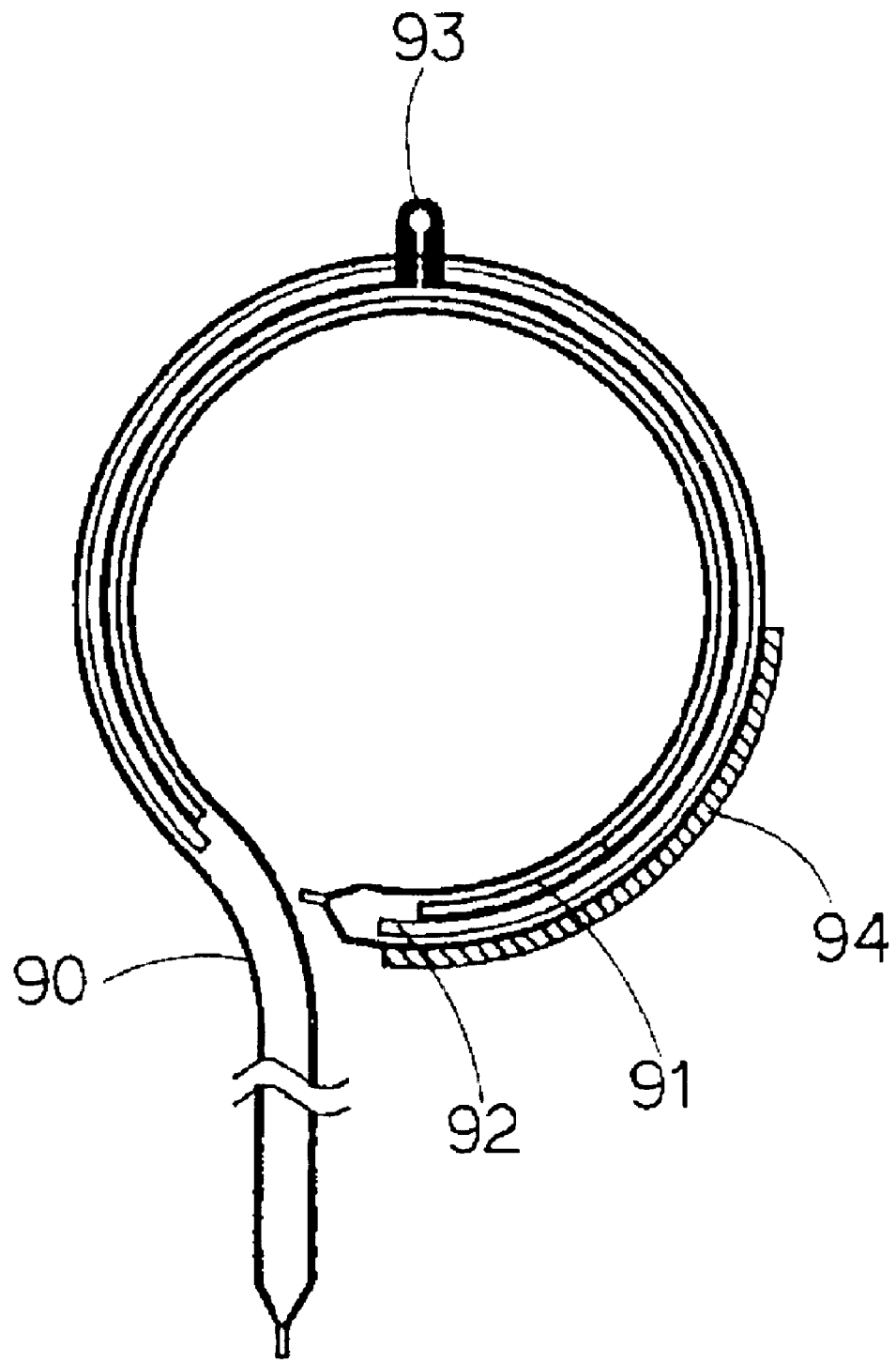
FIG. 12 is a sectional view showing the inside of the cuff of FIG. 11.
Figure 13A:
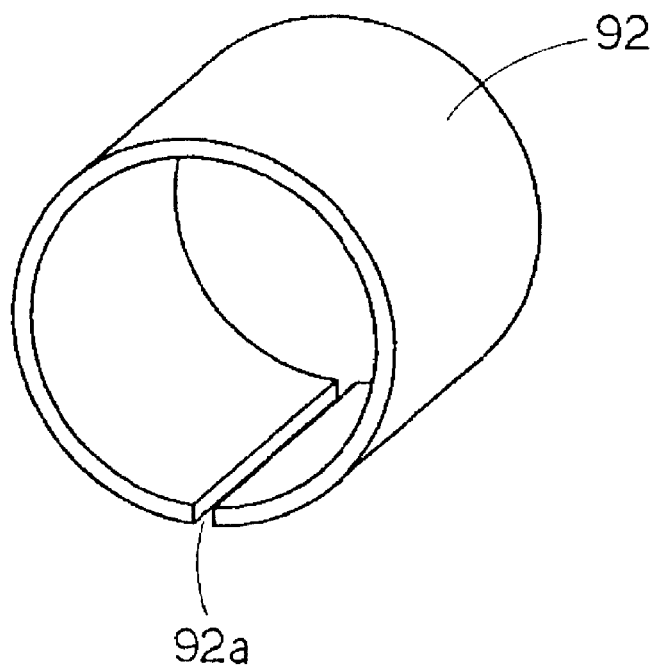
FIG. 13A is a perspective view of a curled elastic member according to a conventional technique, disposed in the cuff of FIG. 11
Figure 13B:
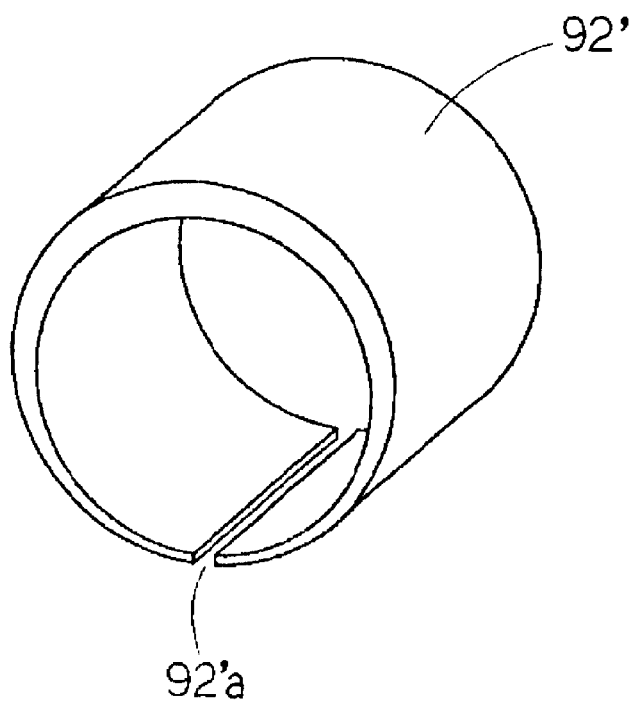
FIG. 13B is a perspective view of a curled elastic member according to another conventional technique.

The present invention will be described below on the basis of embodiments. However, the present invention is characterized by a curled elastic member in a cuff for a blood pressure monitor. Since the structure of the cuff may be an ordinary one shown in FIG. 12, the curled elastic member will be mainly described below. The description of the action of the curled elastic member is applied as it is to the cuff having the curled elastic member.

Figure 1A:
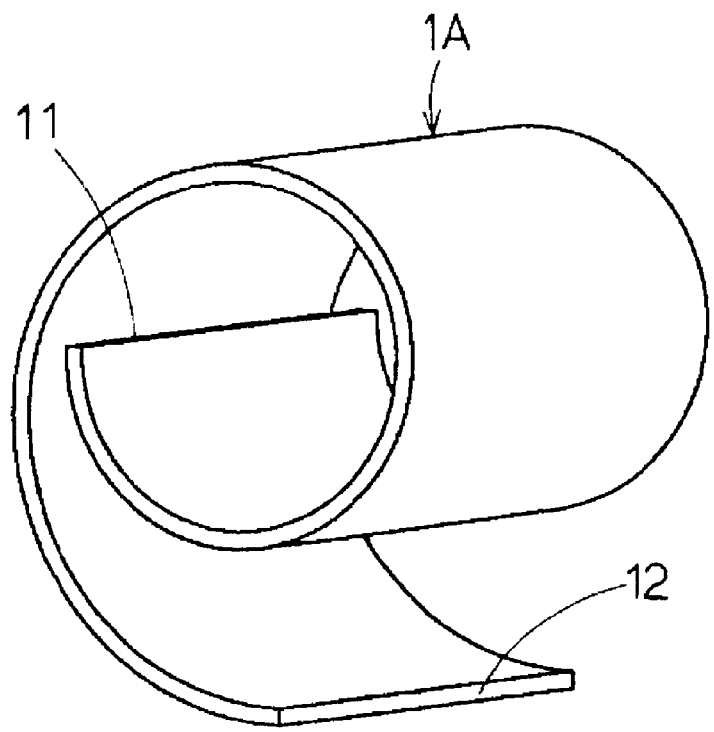
FIG. 1A is a perspective view of a curled elastic member according to an embodiment, provided for a cuff for a blood pressure monitor.
Figure 1B:
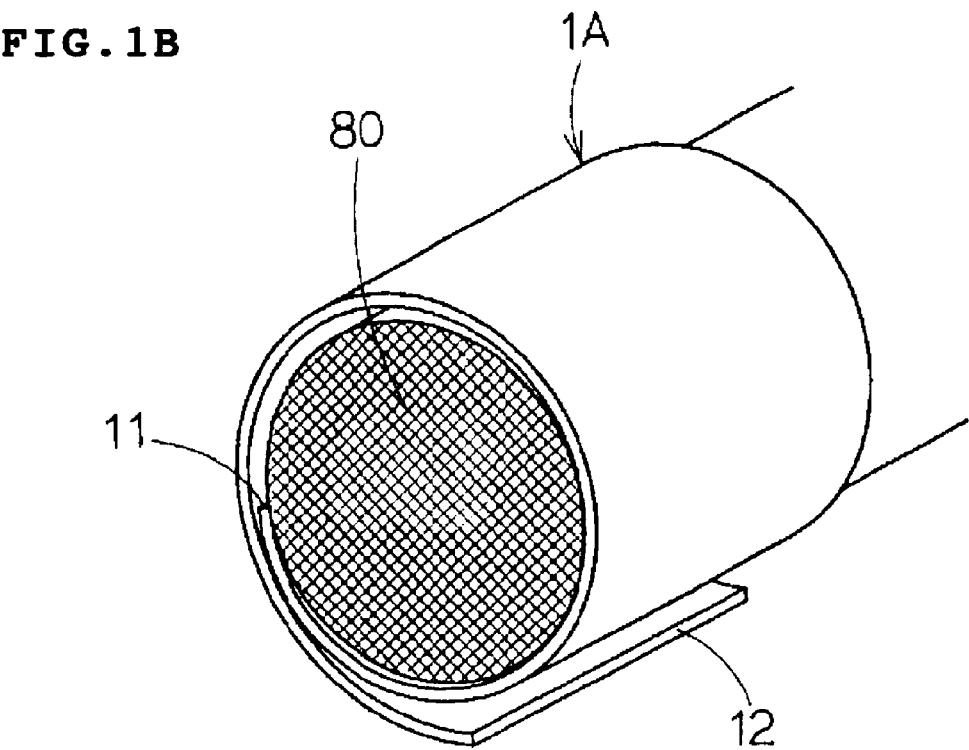
FIG. 1B is a perspective view showing a state where the curled elastic member is attached on an arm.

FIG. 1A is a perspective view of a curled elastic member, according to an embodiment, provided for a cuff for a blood pressure monitor, and FIG. 1B is a perspective view when the curled elastic member is attached to an arm. One end 12 of this curled elastic member 1A is extended outward so as to enwind the other end 11 inward. That is, from the other end 11 to the mid portion of the curled elastic member where the other end 11 meets the curled elastic member, the radius of curvature of the curled elastic member gently increases. From the mid portion of the curled elastic member to the one end 12, the radius of curvature largely increases.

Figure 2A:
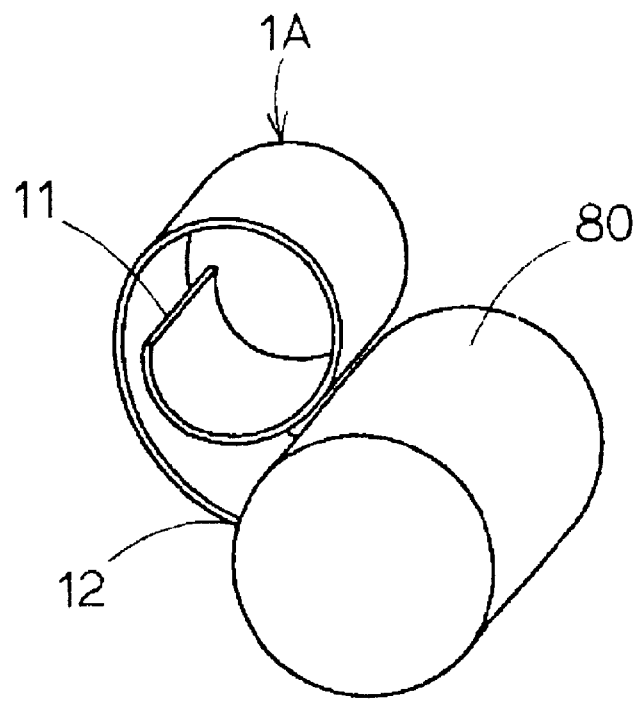
FIGS. 2A and 2B are perspective views showing a first step and a second step, respectively, of attaching the curled elastic member of FIGS. 1A and 1B onto an arm.
Figure 2B:
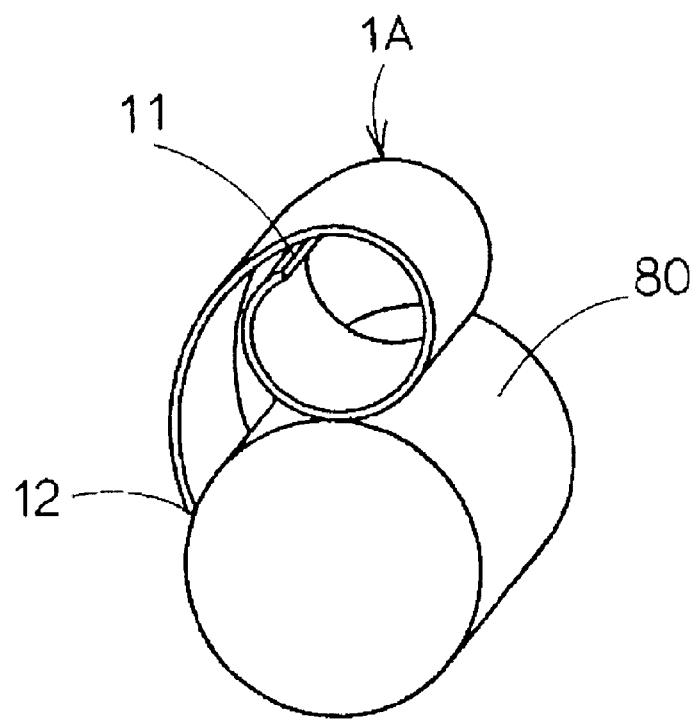
Figure 3A:
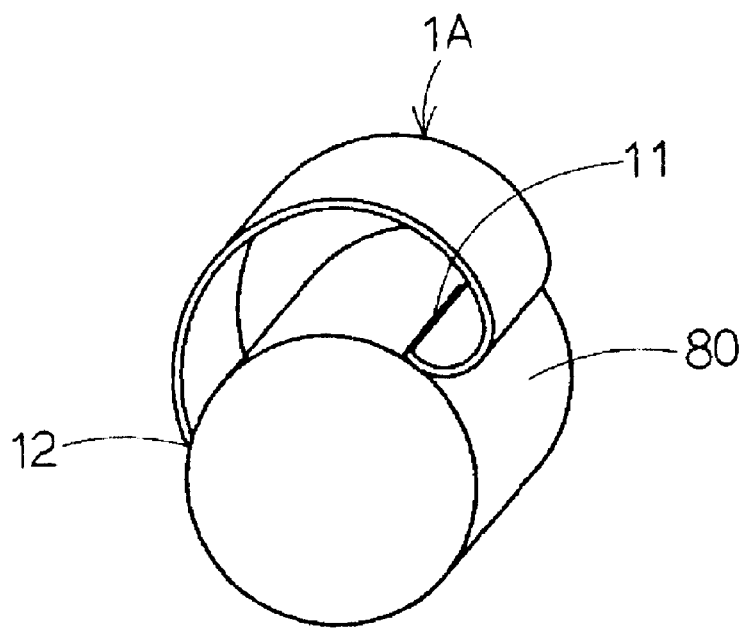
FIG. 3A is a perspective view showing a third step of attaching the curled elastic member of FIGS. 1A and 1B onto an arm.
Figure 3B:
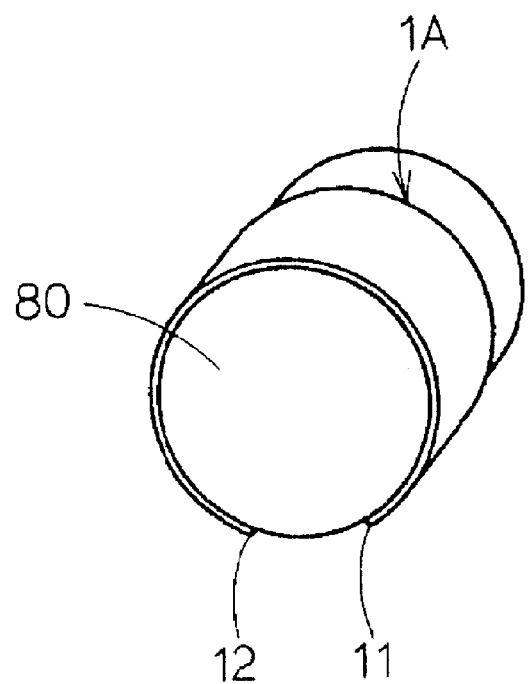
FIG. 3B is a perspective view showing an attached state.

A method of attaching the curled elastic member 1A around an arm 80 will be described by referring to FIGS. 2A and 2B and FIGS. 3A and 3B. First, in FIG. 2A, the one end portion 12 as a longer one of the curved elastic member 1A is thrown over the arm 80. In this state, while uncurling the curled elastic member 1A, it is pulled to the side opposite to the one end portion 12 (FIG. 2B). The curled elastic member 1A is further pulled until the width of the uncurled width becomes about equal to that of the arm 80 (FIG. 3A), the curled elastic member 1A is put on the arm 80 (FIG. 3B). The curled elastic member 1A is then fit to the arm 80 by its elasticity. In such a manner, the curled elastic member 1A, i.e., the cuff is attached on the arm.

When the curled elastic member 1A is used, the operation of uncurling the curled elastic member 1A and the operation of attaching the curled elastic member 1A onto the arm 80 can be simultaneously performed, so that the operation of attaching the curled elastic member 1A onto the arm 80 is easy. Since the one end portion 12 is longer than the other end portion 11 and the other end portion 11 is enwinded inward, when the curled elastic member 1A is attached on the arm 80, the other end portion 11 and the one end portion 12 do not easily cut into the arm 80, and the subject does not feel pain.

Figure 4A:
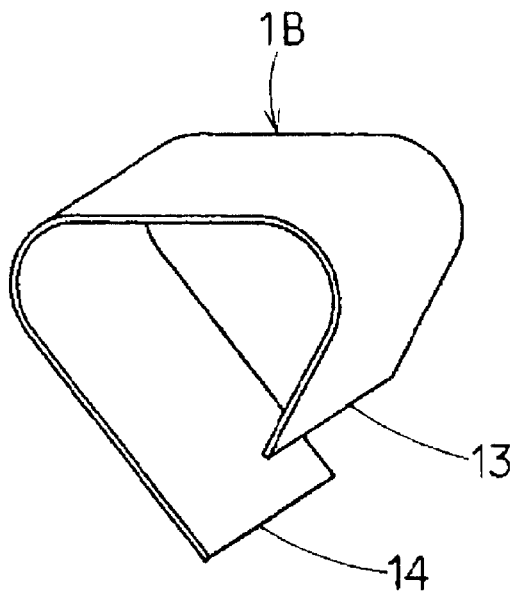
FIG. 4A is a perspective view of a curled elastic member according to another embodiment.

FIG. 4A is a perspective view of a curled elastic member according to another embodiment. This curled elastic member 1B has a sectional shape of approximately triangle and has an extended one end portion 14. The curled elastic member 1B can be attached onto the arm 80 in a manner similar to the above-mentioned curled elastic member 1A. That is, the one end portion 14 which is the longer one of the curled elastic member 1B is thrown over the arm 80, the curled elastic member 1B is pulled to be uncurled and put on the arm 80. Consequently, the operation of uncurling the curled elastic member 1B and the operation of attaching the curled elastic member 1B on the arm 80 can be simultaneously performed.

Figure 4B:
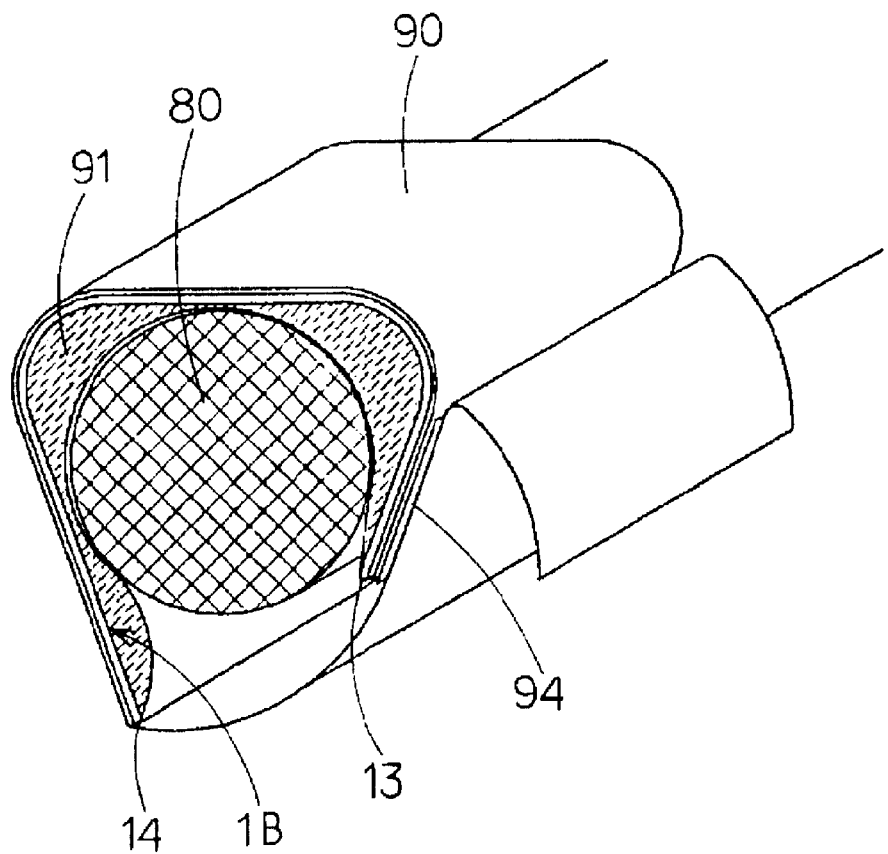
FIG. 4B is a perspective view showing a state where a cuff having the curled elastic member is attached on an arm.

When the curled elastic member 1B whose sectional shape is approximately triangle is attached on the arm 80, as shown in FIG. 4B, a gap is formed between each of the corners and the arm 80. However, the bladder 91 is inflated so as to fill the gap by injection of air, so that the action of pressing the arm 80 with the bladder 91 is not hindered. The sectional shape of the curled elastic member 1B may be, besides approximately triangle, quadrangle or polygon.

Figure 5A:
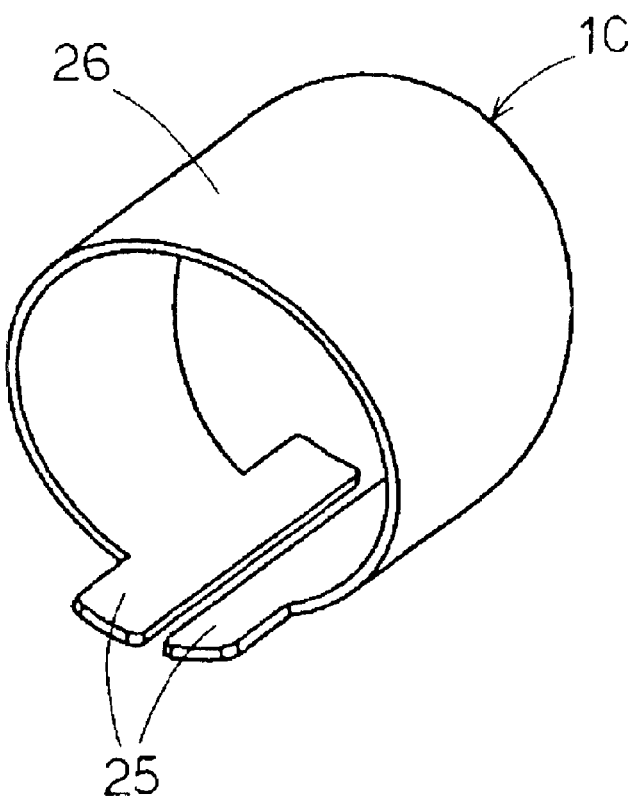
FIGS. 5A and 5B are a perspective view and an exploded view, respectively, of a curled elastic member according to further another embodiment.
Figure 5B:
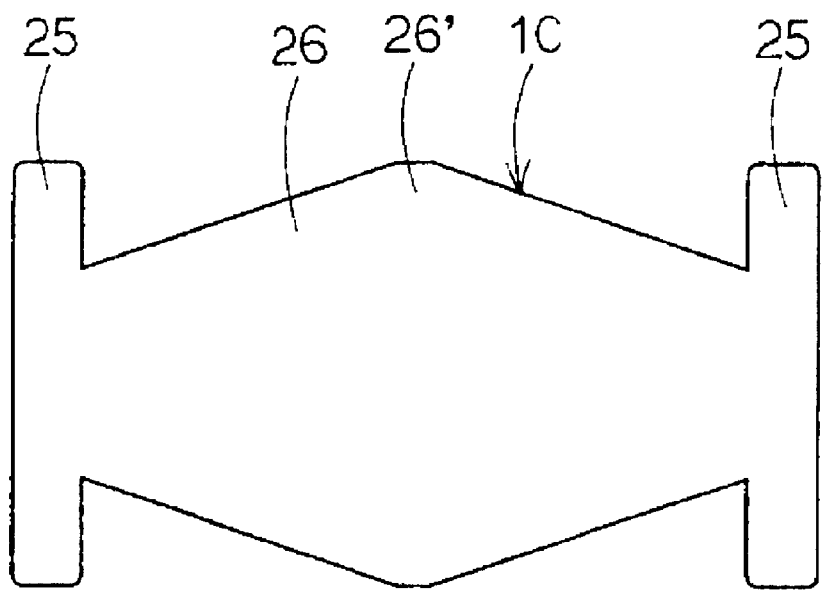

FIGS. 5A and 5B are a perspective view and an exploded view, respectively, of a curled elastic member according to further another embodiment. This curled elastic member 1C has a narrow portion 26 in which a width in the axial direction of an arm is partly narrowed between a center portion 26' in the circumferential direction of the arm and both end portions 25. The narrow portion 26 has a width gradually decreased from the center portion 26' towards the both end portions 25. In the curled elastic member 1C, the rigidity of the narrow portion 26 is reduced. Thus, the curled elastic member 1C (i.e., a cuff) gets easily to be twisted, so that it easily fits to an arm of any shape such as a straight arm or tapered arm.

Since the both end portions 25 of the curled elastic member 1C are not formed as the narrow portion 26, the rigidity of the both end portions 25 does not deteriorate, and the arm can be securely held by the both end portions 25. Further, by not making the both end portions 25 as the narrow portion 26, as compared with a case where the both end portions 25 are also formed as the narrow portion 26, the subject does not have strange feeling such that the both end portions 25 cut into the flesh of the arm.

Figure 6A:
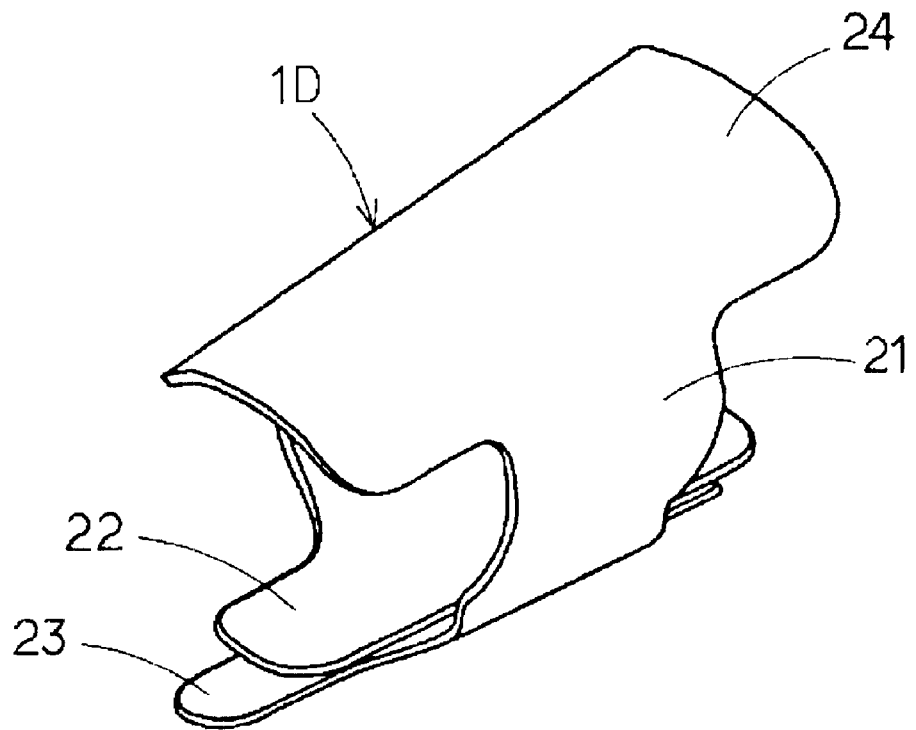
FIGS. 6A and 6B are a perspective view and an exploded view, respectively, of a curled elastic member according to further another embodiment.
Figure 6B:
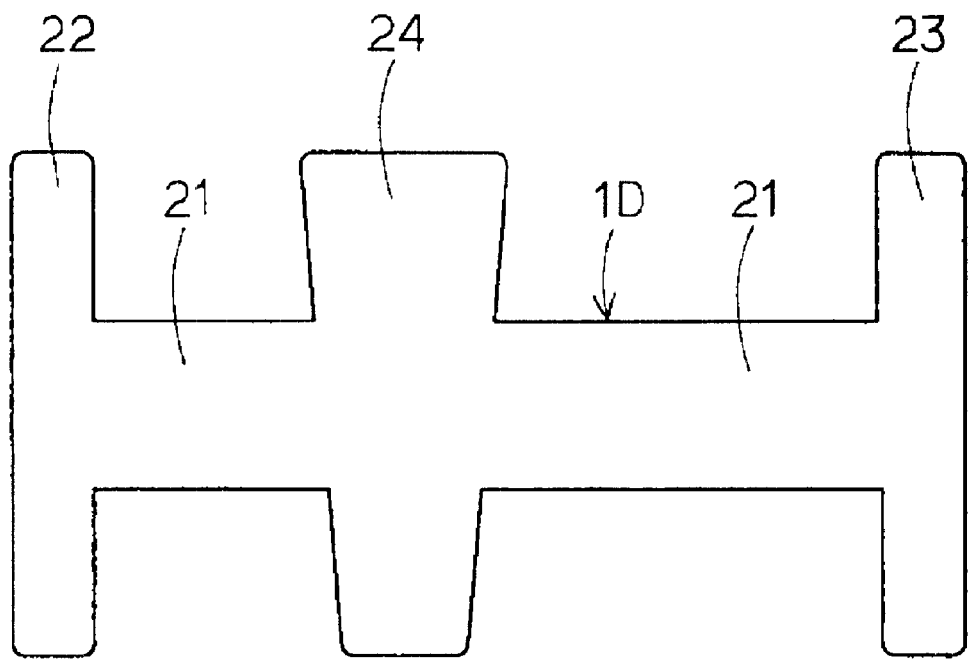

FIGS. 6A and 6B are a perspective view and an exploded view, respectively, of a curled elastic member according to further another embodiment. This curled elastic member 1D has a narrow portion 21 in which a width in the axial direction of an arm is partly narrowed between an approximately center portion 24 in the circumferential direction of the arm and both end portions 22 and 23. The narrow portion 21 has a fixed width in the circumferential direction of the arm. The approximately center portion 24 does not have a fixed width but is tapered in correspondence with an arm which is generally tapered from the shoulder side toward the elbow side. Therefore, at the time of attachment onto an arm, the wider side of the center portion 24 has to be set on the shoulder side. The user has to see the direction of the curled elastic member 1D when it is set in the cloth bag 90 of the cuff. Further, one end portion 23 is extended outward so as to enwind the other end portion 22 inward.

In the curled elastic member 1D, in a manner similar to the curled elastic member 1C, the rigidity of the narrow portion 21 is reduced. Consequently, the curled elastic member ID (i.e., the cuff) gets easily to be twisted, so that it easily fits to an arm of any shape such as a straight arm or tapered arm.

Since the both end portions 22 and 23 of the curled elastic member 1D are not formed as the narrow portion 21, the rigidity of the both end portions 22 and 23 does not deteriorate, and the arm can be securely held by the both end portions 22 and 23. Further, by not making the both end portions 22 and 23 as the narrow portion 21, as compared with a case such that the both end portions 22 and 23 are also formed as the narrow portion 21, the subject does not feel strange such that the both end portions 22 and 23 cut into the flesh of the arm. Obviously, at the time of attachment to an arm, the one end portion 23 which is the longer one is thrown over the arm.

Figure 7A:
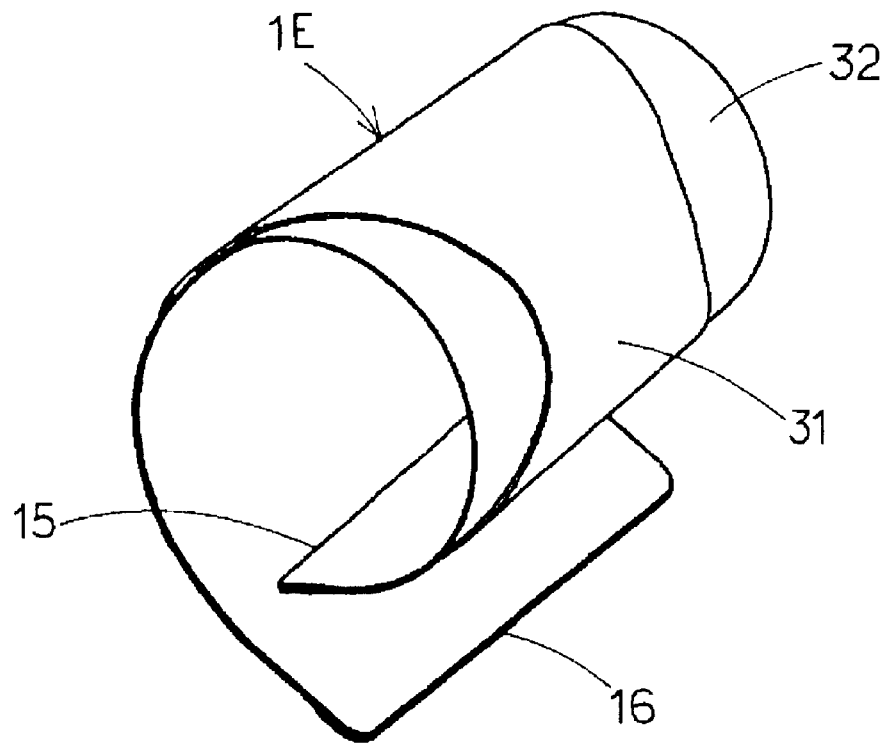
FIGS. 7A and 7B are a perspective view and an exploded view, respectively, of a curled elastic member according to further another embodiment.
Figure 7B:
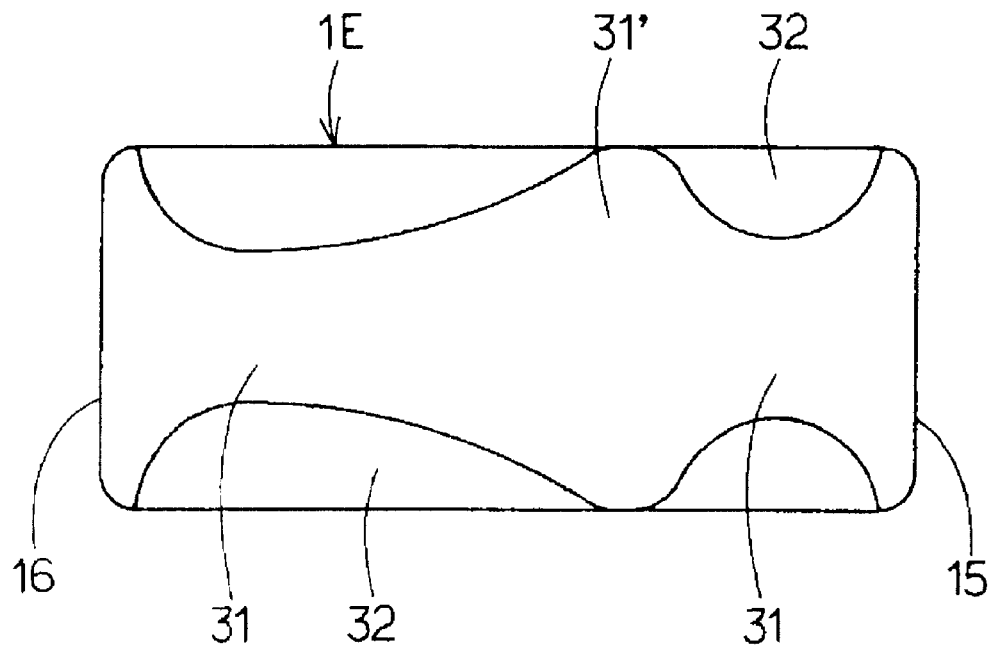

FIGS. 7A and 7B are a perspective view and an exploded view, respectively, of a curled elastic member according to further another embodiment. This curled elastic member 1E has a narrow portion 31 in which a width in the axial direction of an arm is partly narrowed between an approximately center portion 31' in the circumferential direction of an arm and both end portions 15 and 16, and the portion missed by narrowing the width to form the narrow portion 31 is a thin portion 32 which is thinner than the narrow portion 31. The narrow portion 31 has a width which gently increases and decreases from the end portions 15 and 16 toward the center portion 31'. The thin portion 32 exists so as to fill the portion missed by narrowing the width to form the narrow portion 31. Consequently, the curled elastic member 1E as a whole has a fixed width. The one end portion 16 is extended outward so that the other end portion 15 is enwinded inward.

In order to provide the thin portion 32 in the portion missed by narrowing the width to form the narrow portion 31, for example, separately the thin portion 32 as a separate member may be joined to the narrow portion 31 or the portion 32 other than the narrow portion 31 may be formed thin by cutting, integral molding or the like at the time of making the whole curled elastic member 1E. The planar shape pattern of the narrow portion 31 is not limited to that shown in the drawing but, for example, the pattern of the narrow portion 21 in the curled elastic member 1D in FIG. 6 may be used.

The curled elastic member 1E is obtained by improving the curled elastic member 1D. That is, in the case of the form where the portion missed by the narrow portion 31 exists, when the bladder is inflated, it is feared that the bladder is inflated from the side (missing portion) of the narrow portion 31 to the surface side of the cuff so that the arm cannot be sufficiently pressed, and there is also the possibility such that, in a process of taking blood pressure data while changing air pressure, noise occurs due to inflation from the missing portion to the outside of the bladder, so that there is the possibility that blood pressure cannot be measured stably.

However, by forming the missing portion generated due to the narrow portion 31 as the thin portion 32, while maintaining the effects of the curled elastic member 1D, the possibilities of the above-mentioned problems can be also eliminated. That is, by forming the curled elastic member 1D so as to be fit to any of arms of various shapes by the both end portions and so as to be easily twisted, an effect such that the curled elastic member can be easily fit to an arm of any shape such as a straight arm or tapered arm is obtained.

Figure 8A:
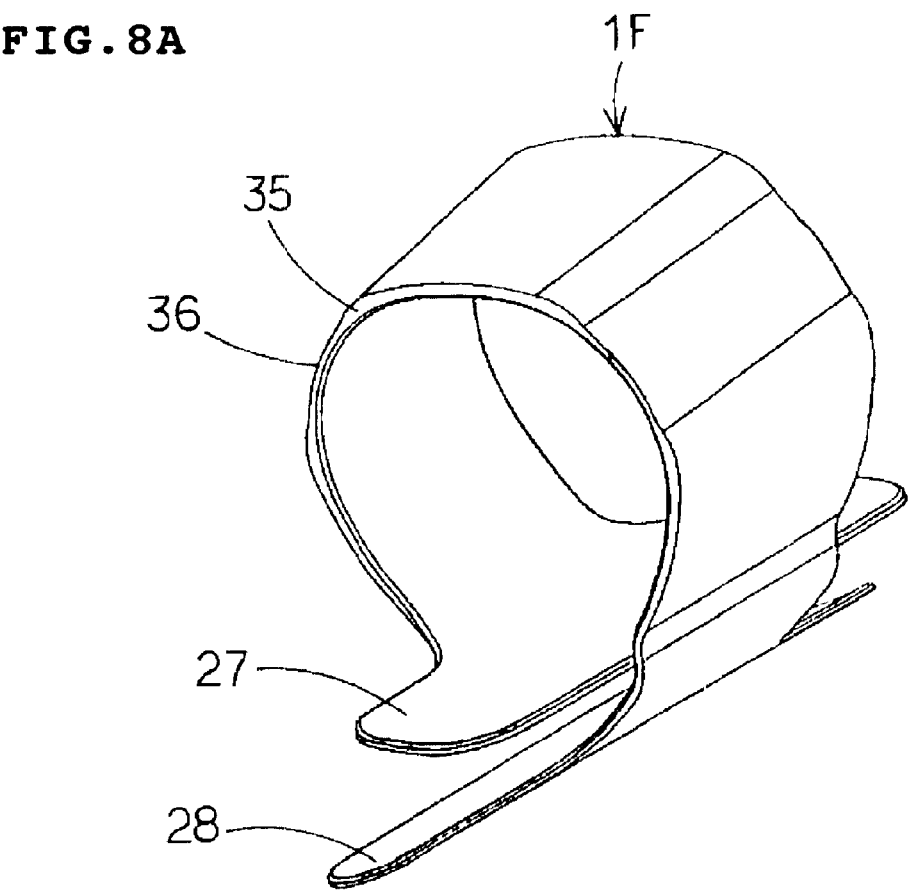
FIGS. 8A and 8B are a perspective view and a sectional view, respectively, of a curled elastic member according to further another embodiment.
Figure 8B:
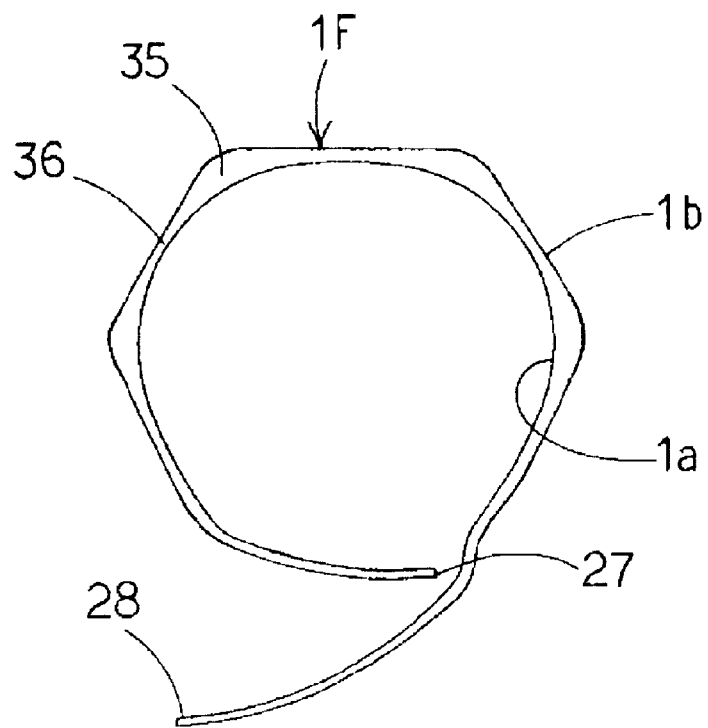

FIGS. 8A and 8B are a perspective view and a sectional view of a curled elastic member according to further another embodiment. This curled elastic member 1F is formed so that its inner circumferential face 1a is an approximately round shape and an outer circumferential face 1b has a polygon shape (approximately hexagon herein). With the structure, the corner portions of the polygon become thick portions 35 and the side portions become thin portions 36. Therefore, the form in which the thickness is changed is obtained as a result. Particularly, in a manner similar to the curled elastic members 1C to 1E, the shape can be altered according to variations in the arm, and the curled elastic member does not easily cut in the arm and fits the arm very well. Obviously, since the one end portion 28 is extended outward than the other end portion 27, the curled elastic member is easily attached on the arm.

Figure 9:
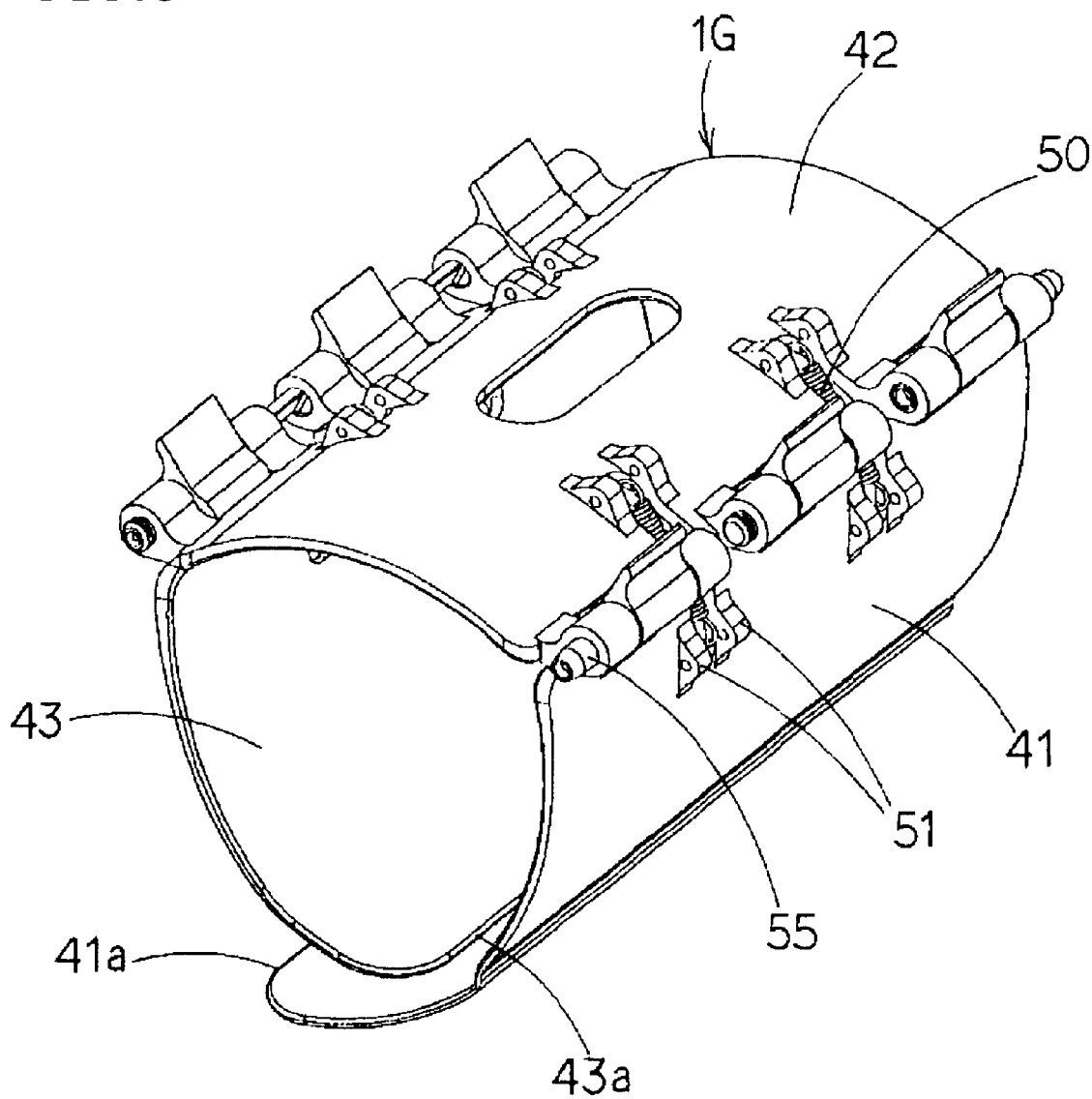
FIG. 9 is a perspective view of a curled elastic member according to further another embodiment.
Figure 11:
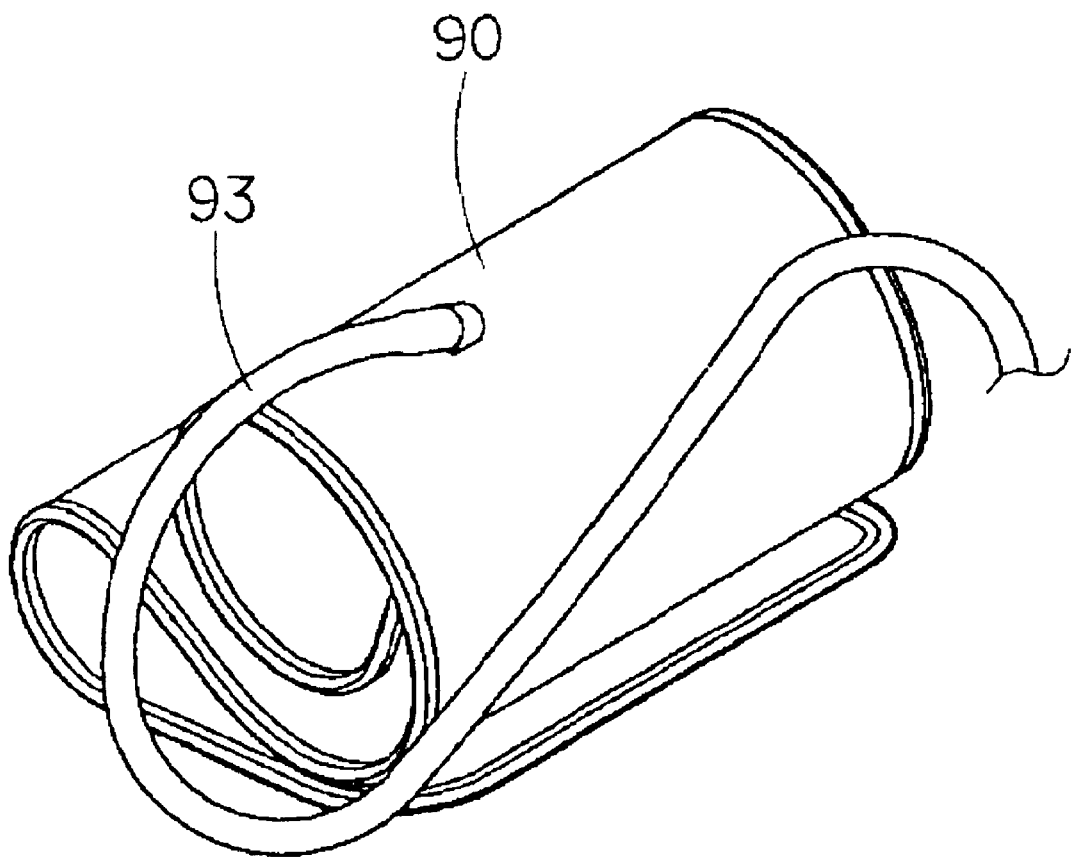
FIG. 11 is a perspective view showing a general cuff.

FIG. 9 is a perspective view of a curled elastic member according to further another embodiment. FIGS. 10A and 10B are side views of the curled elastic member in an uncurled state and in a curled state, respectively. This curled elastic member 1G is formed by connecting a plurality of (three herein) elastic pieces 41, 42, and 43 by hinges. Two coil springs 50 as energizing means are attached to the respective hinged portions. The elastic pieces 41 and 43 serve as both end portions, and the elastic piece 42 serves as a center portion. The elastic piece 41 is set longer than the elastic piece 43 so that an end 43a of the elastic piece 43 is enwinded inward.

Three hinges as the hinged portions are provided between the elastic pieces 41 and 42, and between the elastic pieces 42 and 43. The elastic pieces 41 to 43 can relatively swing around a spindle 55 of each hinged portion as a fulcrum. The coil springs 50 are attached to supporting portions 51 provided at facing ends of the elastic pieces 41 to 43. In each of the elastic pieces 41 to 43, a notch (to which no reference numeral is designated) for receiving the coil spring 50 is formed.

When the curled elastic member 1G is uncurled by a predetermined angle or more, the coil spring 50 is energized in the direction of uncurling the curled elastic member 1G. When the curled elastic member 1G is curled by a predetermined angle or less, the coil spring 50 is energized in the direction of curling the curled elastic member 1G. That is, as obvious from FIGS. 10A and 10B, when the coil spring 50 is positioned on the outer side than the spindle 55 as a fulcrum of each of the elastic pieces 41 to 43, the energizing force acts in the direction of uncurling the curled elastic member 1G (FIG. 10A). When the coil spring 50 is positioned on the inner side than the spindle 55, the energizing force acts in the direction of curling the elastic member 1G (FIG. 10B). However, the curled elastic member 1G is usually in the closed state as shown in FIG. 10B.

When the curled elastic member 1G is attached on an arm, the end portion 41a of the long elastic piece 41 is thrown over the arm and, in such a state, the curled elastic member 1G is uncurled outward at a predetermined angle or more. By the energizing force of the coil spring 50, the curled elastic member 1G naturally enters a maximum uncurled state. When the elastic member 1G is set in a predetermined region of an arm and is curled at a predetermined angle or more, the elastic member 1G is naturally curled by the energizing force of the coil spring 50, and is fit to the arm with a proper pressing force.

As described above, the cuff for the blood pressure monitor of the present invention has the curled elastic member in a peculiar form. Consequently, the cuff can be easily attached to an arm. When the cuff is attached to an arm, the end portions do not easily cut in the flesh of the arm, so that the subject does not feel pain. The shape of the cuff can be altered in correspondence with variations in arms, so that the cuff fits to an arm excellently.

What is claimed is:

1. A cuff for a blood pressure monitor, comprising therein a bladder and a curled elastic member disposed on the outside of the bladder to hold a ring shape of the cuff, wherein one end portion of said curled elastic member is extended outward so as to enwind the other end portion inward.

2. A cuff for a blood pressure monitor, comprising therein a bladder and a curled elastic member disposed on the outside of the bladder to hold a ring shape of the cuff, wherein a sectional shape of said curled elastic member is approximately triangle and one end portion of said curled elastic member is extended.

3. A cuff for a blood pressure monitor, comprising therein a bladder and a curled elastic member disposed on the outside of the bladder to hold a ring shape of the cuff, wherein said curled elastic member has a narrow portion in which a width of said curled elastic member in an axial direction of an arm is partly narrowed between an approximately center portion in a circumferential direction of an arm and both end portions or a thin portion in which a thickness of the curled elastic member is partly reduced between an approximately center portion in a circumferential direction of an arm and both end portions.

4. The cuff for a blood pressure monitor according to claim 3, wherein said curled elastic member has said narrow portion, and wherein said curled elastic member further comprises an additional portion thinner than said narrow portion to fill in a portion of an open space created by narrowing the width of said curled elastic member.

5. The cuff for the blood pressure monitor according to claim 3 or 4, wherein said narrow portion is formed by gradually reducing the width from said center portion toward both end portions.

6. A cuff for a blood pressure monitor, comprising therein a bladder and a curled elastic member disposed on the outside of the bladder to hold a ring shape of the cuff, wherein an inner circumferential face of said curled elastic member has an approximately round shape and an outer circumferential face of said curled elastic member has an approximately polygon shape.

7. A cuff for a blood pressure monitor, comprising therein a bladder and a curled elastic member disposed on the outside of the bladder to hold a ring shape of the cuff, wherein said curled elastic member is formed by connecting a plurality of elastic pieces by hinges, and energizing means for energizing the elastic member in a direction of uncurling the elastic member when the elastic member is uncurled at a predetermined angle or more, and energizing the elastic member in a direction of curling the elastic member when the elastic member is curled at a predetermined angle or less is provided on the hinged portions of the respective elastic pieces.

* * * * *